United States Patent
Damadian

(10) Patent No.: US 12,220,204 B1
(45) Date of Patent: Feb. 11, 2025

(54) HYDRODYNAMIC ENCEPHALOPATHY DETECTION METHOD AND SYSTEM

(71) Applicant: Fonar Corporation, Melville, NY (US)

(72) Inventor: Raymond V. Damadian, Woodbury, NY (US)

(73) Assignee: Fonar Corporation, Melville, NY (US)

( * ) Notice: Subject to any disclaimer, the term of this patent is extended or adjusted under 35 U.S.C. 154(b) by 1038 days.

(21) Appl. No.: 17/173,365

(22) Filed: Feb. 11, 2021

Related U.S. Application Data

(63) Continuation-in-part of application No. 15/596,739, filed on May 16, 2017, now abandoned.

(60) Provisional application No. 62/337,285, filed on May 16, 2016.

(51) Int. Cl.
| | |
|---|---|
| A61B 5/00 | (2006.01) |
| A61B 5/03 | (2006.01) |
| A61B 5/055 | (2006.01) |
| G06T 7/00 | (2017.01) |
| G16H 30/40 | (2018.01) |
| G16H 50/20 | (2018.01) |
| G16H 50/30 | (2018.01) |

(52) U.S. Cl.
CPC ............ *A61B 5/0042* (2013.01); *A61B 5/031* (2013.01); *A61B 5/055* (2013.01); *A61B 5/702* (2013.01); *A61B 5/7275* (2013.01); *A61B 5/7278* (2013.01); *A61B 5/7285* (2013.01); *G06T 7/0014* (2013.01); *G16H 30/40* (2018.01); *G16H 50/20* (2018.01); *G16H 50/30* (2018.01); *A61B 2576/026* (2013.01); *G06T 2207/10088* (2013.01); *G06T 2207/30048* (2013.01)

(58) Field of Classification Search
CPC ....... A61B 5/031; A61B 5/055; A61B 5/4076; A61B 5/4836
See application file for complete search history.

(56) References Cited

U.S. PATENT DOCUMENTS

| | | |
|---|---|---|
| 6,369,571 B1 | 4/2002 | Damadian et al. |
| 6,414,490 B1 | 7/2002 | Damadian et al. |
| 6,677,753 B1 | 1/2004 | Danby et al. |
| 8,401,162 B2 | 3/2013 | Sakata et al. |
| 8,834,387 B2 | 9/2014 | Platt |
| 9,504,429 B1 | 11/2016 | Minkoff |
| 9,649,047 B1 | 5/2017 | Damadian et al. |
| 2004/0251722 A1 | 12/2004 | Boyle |
| 2007/0232894 A1 | 10/2007 | Feenan |
| 2014/0373278 A1 | 12/2014 | Scott et al. |
| 2016/0058319 A1 | 3/2016 | Shiodera et al. |

OTHER PUBLICATIONS

Damadian et al., The Possible Role of Cranio-Cervical Trauma and Abnormal CSF Hydrodynamics in the Genesis of Multiple Sclerosis, Physiol. Chem. Phys. & Med. NMR, 41, pp. 1-17, Sep. 2011.

*Primary Examiner* — Mark D Remaly
(74) *Attorney, Agent, or Firm* — Lerner David LLP

(57) ABSTRACT

A method for assessing a risk of cerebral palsy in a subject based on cerebrospinal fluid (CSF) flow of a subject in which magnetic resonance imaging signals of a selected region of interest of the subject's anatomy are acquired. Preferably, the selected region of interest comprises the cerebro-spinal anatomy and acquisition of the signals is triggered by a cardiac signal.

23 Claims, 7 Drawing Sheets

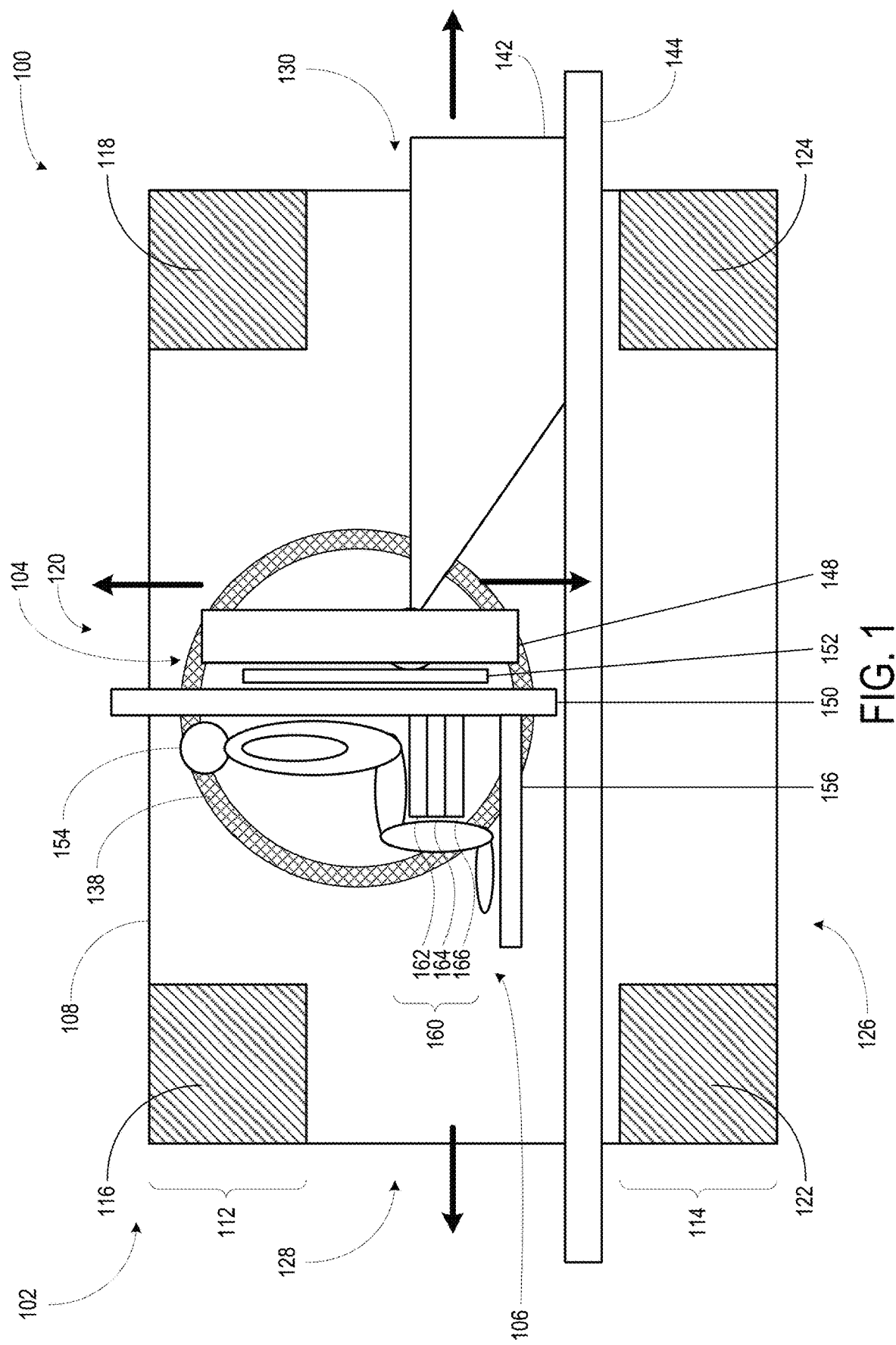

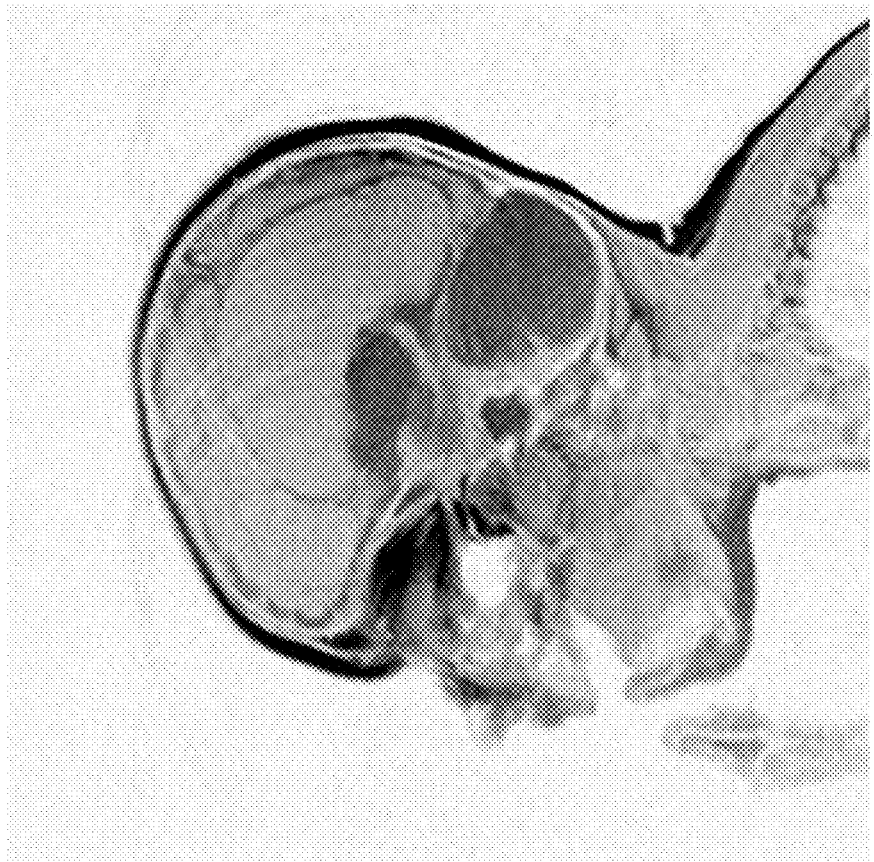
FIG. 5A

HYDRODYNAMIC ENCEPHALOPATHY DETECTION METHOD AND SYSTEM

CROSS-REFERENCE TO RELATED APPLICATIONS

The present application is a continuation-in-part of U.S. patent application Ser. No. 15/596,739, filed on May 16, 2017, which claims the benefit of the filing date of U.S. Provisional Patent Application No. 62/337,285 filed May 16, 2016, the disclosures of which are incorporated herein by reference.

TECHNICAL FIELD

The present disclosure relates to magnetic resonance imaging apparatus, systems and methods and procedures for improved measurement and quantification of Cerebro-Spinal Fluid ("CSF") flow to allow for risk assessment of Cerebral Palsy.

BACKGROUND

In magnetic resonance imaging, an object to be imaged such as, for example, a body of a human subject, is exposed to a strong, substantially constant static magnetic field. Radio frequency excitation energy is applied to the body, and this energy causes the spin vectors of certain atomic nuclei within the body to rotate or "precess" around axes parallel to the direction of the static magnetic field. The precessing atomic nuclei emit weak radio frequency signals during the relaxation process, referred to herein as magnetic resonance signals. Different tissues produce different signal characteristics. Furthermore, relaxation times are the major factor in determining signal strength. In addition, tissues having a high density of certain nuclei will produce stronger signals than tissues with a low density of such nuclei. Relatively small gradients in the magnetic field are superimposed on the static magnetic field at various times during the process so that magnetic resonance signals from different portions of the patient's body differ in phase and/or frequency. If the process is repeated numerous times using different combinations of gradients, the signals from the various repetitions together provide enough information to form a map of signal characteristics versus location within the body. Such a map can be reconstructed by conventional techniques well known in the magnetic resonance imaging art, and can be displayed as a pictorial image of the tissues as known in the art.

The magnetic resonance imaging technique offers numerous advantages over other imaging techniques. MRI does not expose either the patient or medical personnel to X-rays and offers important safety advantages. In addition, magnetic resonance imaging can obtain images of soft tissues and other features within the body which are not readily visualized using other imaging techniques. Accordingly, magnetic resonance imaging has been widely adopted in the medical and allied arts.

Several factors impose significant physical constraints in the positioning of patients and ancillary equipment in MRI imaging. Many MRI magnets use one or more solenoidal superconducting coils to provide the static magnetic field arranged so that the patient is disposed within a small tube running through the center of the magnet. The magnet and tube typically extend along a horizontal axis, so that the long axis or head-to-toe axis of the patient's body must be in a horizontal position during the procedure. Moreover, equipment of this type provides a claustrophobic environment for the patient. Iron core magnets have been built to provide a more open environment for the patient. These magnets typically have a ferromagnetic frame with a pair of ferromagnetic poles disposed one over the other along a vertical pole axis with a gap between them for receiving the patient. The frame includes ferromagnetic flux return members such as plates or columns extending vertically outside of the patient-receiving gap. A magnetic field is provided by permanent magnets or electromagnetic coils associated with the frame. A magnet of this type can be designed to provide a more open environment for the patient. However, it is still generally required for the patient to lie with his or her long axis horizontal.

Recently, ferromagnetic frame magnets having horizontal pole axes have been developed. As disclosed, for example, in commonly assigned U.S. Pat. Nos. 6,414,490, 6,369,571 and 6,677,753, the disclosures of which are incorporated by reference herein, a magnet having poles spaced apart from one another along a horizontal axis provides a horizontally oriented magnetic field within a patient-receiving gap between the poles. Such a magnet can be used with a patient-positioning device including elevation and tilt mechanisms to provide extraordinary versatility in patient positioning. For example, where the patient positioning device includes a bed or similar device for supporting the patient in a recumbent position, the bed can be tilted and/or elevated so as to image the patient in essentially any position between a fully standing position and a fully recumbent position, and can be elevated so that essentially any portion of the patient's anatomy is disposed within the gap in an optimum position for imaging. As further disclosed in the previously mentioned patents, the patient positioning device may include additional elements such as a platform projecting from the bed to support the patient when the bed is tilted towards a standing orientation. Still other patient supporting devices can be used in place of a bed in a system of this type. For example, a seat may be used to support a patient in a sitting position. Thus, magnets of this type provide extraordinary versatility in imaging.

Cerebrospinal fluid ("CSF") is a clear body fluid found in the brain and spine. It provides mechanical and immunological protection to the brain, as well as cerebral autoregulation of cerebral blood flow. While references by ancient physicians, e.g., Hippocrates and Galen, to "water" or "liquid" surrounding or within the brain, suggest awareness of CSF for millennia, in recent years its study has taken on renewed importance. For example, in a Sep. 20, 2011, paper entitled "The Possible Role of Cranio-Cervical Trauma and Abnormal C SF Hydrodynamics in the Genesis of Multiple Sclerosis" and published in Physiological Chemistry and Physics and Medical NMR, Vol. 41: 1-17, Damadian and Chu uncovered a key set of new observations regarding the possible relationship between CSF flow and Multiple Sclerosis (MS). In their work, Damadian and Chu conducted MRI studies of CSF flow in several patients observing that the "obstruction to CSF outflow would result in an increase in ventricular CSF pressure (ICP) which in turn could result in 'leakage' of cerebrospinal fluid and its content . . . ." The importance of understanding the relationship between CSF flow, velocity, volume, etc. and a variety of physical and/or neurological maladies cannot be overstated. As such, systems and methods that can better enable that understanding are extremely important to the medical profession.

As such, needs arise that require improvement in MRI technology, including software and related hardware. For example, while MRI captures tissue contrasts, improvements are needed to enable real time quantification of CSF flow in the cerebro-spinal anatomy.

SUMMARY

The present disclosure is directed to methods and system or apparatus that measures and/or determine cerebrospinal fluid (CSF) flow within a selected region of anatomy. In one aspect, the method measures CSF flow of a subject and based on that measurements assesses the risk or likelihood of cerebral palsy in the subject.

An example of the inventive technology includes a method detecting cerebrospinal fluid (CSF) flow of a subject for assessment of risk for cerebral palsy.

The method includes: acquiring magnetic resonance imaging data of a selected region of interest of the subject's anatomy by the magnetic resonance imaging apparatus; measuring CSF flow using the acquired magnetic resonance imaging data to obtain CSF flow measurements; and processing the acquired magnetic resonance imaging signals to assess the risk of cerebral palsy in the subject, wherein the processing includes comparing the CSF flow measurements to respective predetermined ranges of CSF flow measurement values.

In accordance with this or other examples, the method further comprises receiving one or more signals from a cardiac triggering device coupled to the subject, wherein the cardiac triggering device comprises any one of an electrocardiogram, plethysmograph, or ultrasound cardiogram.

In accordance with this or other examples, the CSF flow measurements include any one or combination of peak systolic CSF flow velocity, peak diastolic CSF flow velocity, peak systolic CSF flow rate, peak diastolic CSF flow rate, peak-to-peak pressure gradient, peak systolic pressure gradient, peak diastolic pressure gradient, and CSF area. Comparing the CSF flow measurements to respective predetermined ranges of CSF flow measurement values comprises determining, for each CSF flow measurement, whether the CSF flow measurement is within the predetermined range of a corresponding CSF flow measurement value, wherein a greater number of CSF flow measurements being outside the respective predetermined ranges of CSF flow measurement values is indicative of a greater likelihood of the risk of cerebral palsy in the subject. Additionally or alternatively, processing the acquired magnetic resonance imaging signals comprises processing the CSF flow measurements as a sequence of images for display.

In accordance with this or other examples, the subject is positioned in an upright position or a recumbent position in the magnetic resonance imaging apparatus. The subject may be a neonate seated in a car seat compatible with the magnetic resonance imaging apparatus.

In accordance with this or other examples, the cerebrospinal anatomy comprises one or more locations in the CSF circulatory system. The CSF circulatory system may comprise any one of the spinal cord, mid-C2 vertebral level and the Aqueduct of Sylvius.

Another example of the technology presently disclosed includes a system for assessing a risk of cerebral palsy in a subject. The system includes: a magnetic resonance imaging apparatus configured to trigger acquisition of magnetic resonance imaging signals of a selected region of interest of the subject's anatomy based on the cardiac cycle triggering signals; a memory storing instructions; and a processor programmed using the instructions and configured to: receive the acquired magnetic resonance imaging signals, measure CSF flow using the acquired magnetic resonance imaging data to obtain CSF flow measurements, and determine the risk of cerebral palsy in the subject by comparing the CSF flow measurements to respective predetermined ranges of CSF flow measurements.

In accordance with this or other examples, the processor may measure any one or combination of peak systolic CSF flow velocity, peak diastolic CSF flow velocity, peak systolic CSF flow rate, peak diastolic CSF flow rate, peak-to-peak pressure gradient, peak systolic pressure gradient, peak diastolic pressure gradient, and CSF area.

In accordance with this or other examples, the processors may compare the CSF flow measurements to respective predetermined ranges of CSF flow measurements and determine, for each CSF flow measurement, whether the CSF flow measurement is within the predetermined range of a corresponding CSF flow measurement value, wherein a greater number of CSF flow measurements being outside the respective predetermined ranges of CSF flow measurement values is indicative of a greater likelihood of the risk of cerebral palsy in the subject.

In accordance with this or other examples, the processor may process the CSF flow measurements for display as a sequence of images.

In accordance with this or other examples, the apparatus includes a pair of magnetic poles spaced apart along a first direction parallel to a support surface of the apparatus, wherein the magnetic poles are configured to create a magnetic field in the first direction, and wherein the apparatus is adapted to accommodate the subject between the poles while the subject is in an upright position. The apparatus may be adapted to accommodate the subject while the subject is positioned in an upright position or a recumbent position. Additionally or alternatively, the apparatus may be adapted to accommodate a neonate subject while the subject is positioned is seated in a car seat compatible with the magnetic resonance imaging apparatus.

In accordance with this or other examples, the selected region of interest in the subject's anatomy comprises one or more locations in the CSF circulatory system. The CSF circulatory system may include any one of the spinal cord, mid-C2 vertebral level and the Aqueduct of Sylvius.

In accordance with this or other examples, the system may comprise a triggering device coupled to the subject and configured to generate cardiac cycle triggering signals associated with a timing of the subject's cardiac function, wherein the cardiac triggering device comprises any one of an electrocardiogram, plethysmograph, or ultrasound cardiogram.

Yet another example of the technology presently disclosed includes a method for assessing risk for cerebral palsy in a subject. The method includes: acquiring magnetic resonance imaging data of a selected region of interest of the subject's anatomy by the magnetic resonance imaging apparatus, the selected region of interest comprising the cerebrospinal anatomy; obtaining CSF flow measurements from the acquired magnetic resonance imaging data, wherein the CSF flow measurements includes one or more of CSF flow rate data, CSF flow velocity data, and pressure gradient data; and comparing the obtained CSF flow measurements to respective predetermined ranges of CSF flow measurement values to assess cerebral palsy.

In accordance with this or other examples, the CSF flow measurements include two or more of peak systolic CSF flow velocity, peak diastolic CSF flow velocity, peak systolic CSF flow rate, peak diastolic CSF flow rate, peak-to-peak pressure gradient, peak systolic pressure gradient, peak diastolic pressure gradient, and CSF area. Comparing the obtained CSF flow measurements to respective predetermined ranges of CSF flow measurement values may include determining, for each obtained CSF flow measurement, whether the CSF flow measurement is within the predetermined range of a corresponding CSF flow measurement value, wherein a greater number of CSF flow measurements being outside the respective predetermined ranges of CSF flow measurement values is indicative of a greater likelihood of the risk of cerebral palsy in the subject. Each predetermined range of a CSF flow measurement value may be a 67% interval, whereby boundaries of the range are one standard deviation from a mean of the CSF flow measurement value measured in control subjects that are not suspected of having cerebral palsy. The method may include: receiving one or more signals from a cardiac triggering device coupled to the subject; triggering acquisition of magnetic resonance imaging data of a selected region of interest of the subject's anatomy by the magnetic resonance imaging apparatus based on the one or more signals received from the triggering device, the selected region of interest comprising the cerebro-spinal anatomy; measuring CSF flow using the acquired magnetic resonance imaging data to obtain CSF flow measurements; and processing the acquired magnetic resonance imaging signals to assess cerebral palsy in the subject including comparing the CSF flow measurements to predetermined CSF flow measurement values.

BRIEF DESCRIPTION OF THE DRAWINGS

FIG. 1 illustrates an exemplary MRI apparatus for imaging a subject according to aspects of the technology of the present application.

FIGS. 5A and 5B show MRI images of a subject in accordance with the technology of the present application.

DETAILED DESCRIPTION

Figure 2A:
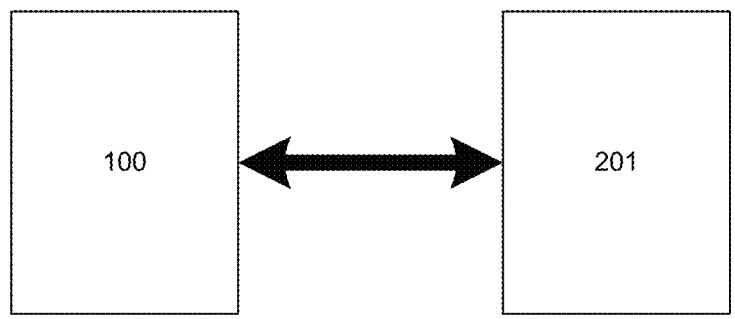
FIG. 2A illustrates a system in accordance with an aspect of the technology of the present application.

The description to follow provides enabling but non-limiting examples of the various aspects of the present disclosure. From these non-limiting examples one skilled in the art will appreciate that the disclosed methods and systems may be modified without departing from the teachings and scope of the claimed invention.

FIG. 1 illustrates an exemplary MRI apparatus 100 for imaging a subject according to aspects of the disclosure. In one embodiment, the MRI apparatus 100 includes a magnet having a ferromagnetic frame 102, a magnetic flux generator 104, and a patient handling system 106. The ferromagnetic frame 102 includes a first side wall 108 and a second side wall. The side walls extend vertically. As FIG. 1 is a sectional view of the MRI apparatus 100, it does not show the second side wall or any of its associated structures for clarity. The second side wall would include all the components necessary to complete the path for a magnetic circuit or loop, e.g., a corresponding pole or an electromagnetic coil assembly to that shown in FIG. 1 with reference numeral 138, etc.

The ferromagnetic frame 102 may also include a top flux return structure 112 and a bottom flux return structure 114. The top flux return structure 112 may include two columnar structures 116 and 118. Between these two columnar structures, a top opening 120 is defined. Similarly, the bottom flux return structure 114 may include two columns 122 and 124 that together define a bottom opening 126. Thus, the side walls and the flux return members 112 and 114 form a rectilinear structure, with the top flux return structure 112 constituting the top wall of the rectilinear structure, the bottom flux return structure 114 constituting the bottom wall of the rectilinear structure and the side walls forming the side walls of the rectilinear structure. The frame 102 defines a front patient opening 128 on one side of the frame and a similar back patient opening 130 on the opposite side of the frame.

The ferromagnetic frame further includes a first magnetic pole and a second magnetic pole. The first magnetic pole extends from the first side wall 108 towards the second side wall and the second magnetic pole extends from the second side wall towards the first side wall 108. The magnetic poles are generally cylindrical and are coaxial with one another on a common horizontal polar axis. Between the magnetic poles is a gap accessed by the front patient opening 128, the back patient opening 130, the top opening 120 or the bottom opening 126.

The magnetic flux generator 104 includes a first electromagnetic coil assembly 138 magnetically coupled to ferromagnetic frame 102, proximate to side 108, and parallel to side 108. The magnetic flux generator 104 also includes a second electromagnet coil assembly (not shown) magnetically coupled to ferromagnetic frame 102, proximate to the second side wall, and parallel to the second side wall. As previously noted, these electromagnetic coil assemblies 138 and 140 may be either resistive or superconductive. Alternatively, the magnetic flux generator 104 may be a permanent magnet. The magnetic flux generator 104 may be configured to emit a magnetic field Bo along one or more axes. The magnetic flux generator 104 may also include one or more gradient coils (not shown) for inducing a gradient in the Bo magnetic field. The Bo magnetic field generally extends horizontally parallel to support surface of the apparatus from one side wall to the other. The support surface will generally be the floor of a building or facility housing the apparatus 100.

The apparatus 100 may further include a patient support assembly 106 including a chair or seat assembly 160 on which a patient is capable of sitting. The patient handling system 106 is capable of three degrees of motion. The patient handling system further supports positioning of a patient in other possible bed angles and orientations, including but not limited to the Trendelburg and reverse-Trendleburg orientations. Generally, the degrees of motion allow for positioning of the patient in a variety of orientations or positions. The patient handling system 106 may include a carriage 142 mounted on rails 144. The carriage 142 may move linearly back and forth along the rails 144. The rails 144 typically do not block the bottom open space 126.

A generally horizontal pivot axis is mounted on carriage 142. An elevator frame 148 is mounted to the pivot axis. The carriage 142 is operable to rotate the elevator frame 148 about the pivot axis. A patient support 150 is mounted on the elevator frame 148. The patient support 150 may be moved linearly along the elevator frame 148 by an actuator 152.

Thus, a patient 154 can be positioned with a total of three degrees of freedom, or along three axes of movement. Specifically, the patient handling system 106 can move a patient 154 in two linear directions and also rotate patient 154 around an axis. The solid black arrows of FIG. 1 show various axes of movement possible with the patient handling system 106. Note that often the rails 108 are mounted such that portions of patient 154 may be positioned below the rails through bottom open space 126.

The apparatus 100 may be configured such that the seat assembly 160 is not present. In that configuration, the patient would then be allowed to stand on the support 156. Allowing the patient to sit or stand, or more generally to remain in an upright position during imaging, has many advantages. For example, blood and CSF flow will be different in the upright position than in a recumbent position and measurements in each position may reveal different information. In addition, upright imaging of CSF properties such as flow may reveal abnormal conditions.

In making MRI measurements, the patient is fitted with an antenna coil that receives magnetic resonance signals from the region of interest of the subject's anatomy being imaged. Such antennas are placed at on or proximate the patient and may include a variety of geometries that maximize the signal strength and signal-to-noise (S/N) ratios of the magnetic resonance signals emitted by the anatomy of interest. Such antennas may include head coils to capture image signals associated with the head, neck or upper spine. Other antennas may include coils that are place proximate the back or spinal column. As another example, the patient support assembly 106 may include a seat assembly 160 may include a quadrature coil arrangement. In particular, the seat assembly 160 may include a seat or sitting surface 166, an enclosure 162 containing a contoured quadrature coil, and a cushion 164. The enclosure 162, which is shown as being adjacent to patient 154, may then the contoured quadrature coil having a normal vector transverse to the horizontal pole axis of the magnetic poles of the MRI apparatus 100, and thus transverse to the magnetic field vector parallel to the horizontal pole axis.

Additional views and disclosure of an MRI apparatus of the type discussed above may be found by reference to U.S. Pat. No. 6,677,753, the disclosure of which is incorporated herein by reference. Alternative embodiments of the MRI apparatus also include those discussed in U.S. Pat. No. 6,414,490, the disclosure of which is also incorporated by reference. In addition, the magnetic resonance image apparatus does not necessarily need to include ferromagnetic frames or poles. For example, an apparatus such as that disclosed in commonly assigned U.S. Pat. No. 8,384,387, the disclosure of which is incorporated by reference herein, may comprise the magnetic resonance imaging apparatus in accordance with the various aspects of the present invention.

Turning now to FIG. 2A, there is shown a high level block diagram of a system 200 that includes the apparatus 100 and a computing device 201. The computing device 201 is programmed using instructions that cause it to receive magnetic resonance imaging signals from the apparatus 100 and process those signals to determine an outline associated with the anatomy of interest, and use the outline to control detection and/or measurement of CSF flow in an area adjacent to the anatomy of interest or otherwise associated with the subject's anatomy.

Figure 2B:
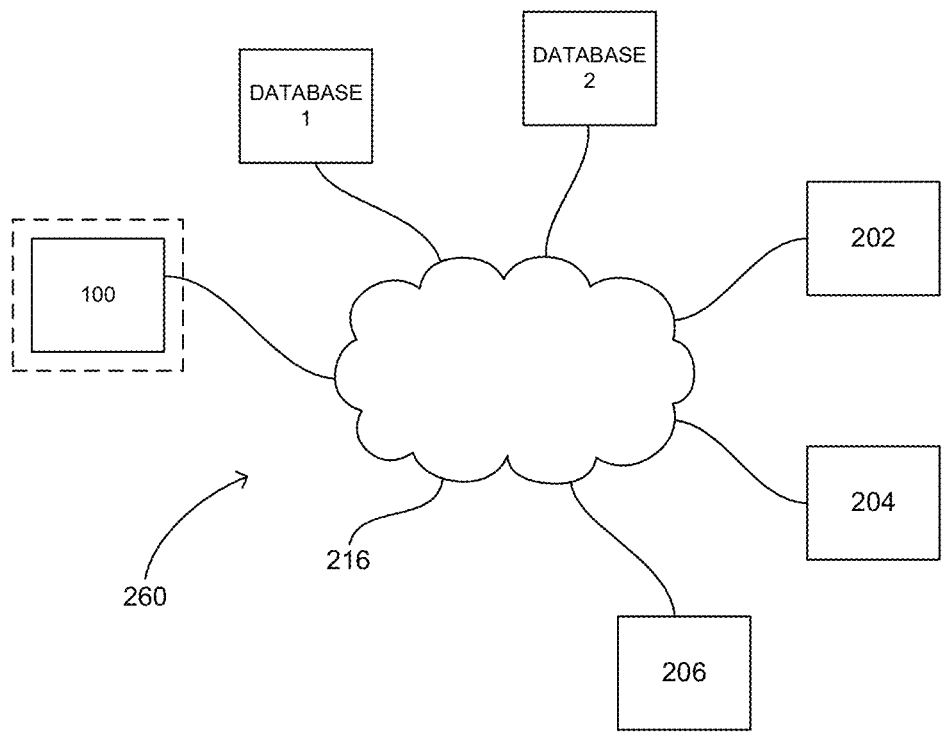
FIG. 2B illustrates a networked system in accordance with an aspect of the technology of the present application.

The system 200 may be part of a computer network as shown in FIG. 2B. The illustration of FIG. 2B presents a schematic diagram of a computer system depicting various computing devices that can be used alone or in a networked configuration in accordance with aspects of the invention. For example, this figure illustrates a computer network 260 having a plurality of computers 202, 204 and 206. The network 260 may include other types of devices such as mobile phones or PDAs. Various elements in the computer network 260 may be interconnected via a local or direct connection (such as shown in FIG. 2A) and/or may be coupled via a communications network 216 such as a local area network ("LAN"), a WiFi network, a wide area network ("WAN"), the Internet, etc. and which may be wired or wireless. The communications network 216 may include a plurality of nodes having routers, servers, wireless access points, etc.

Figure 2C:
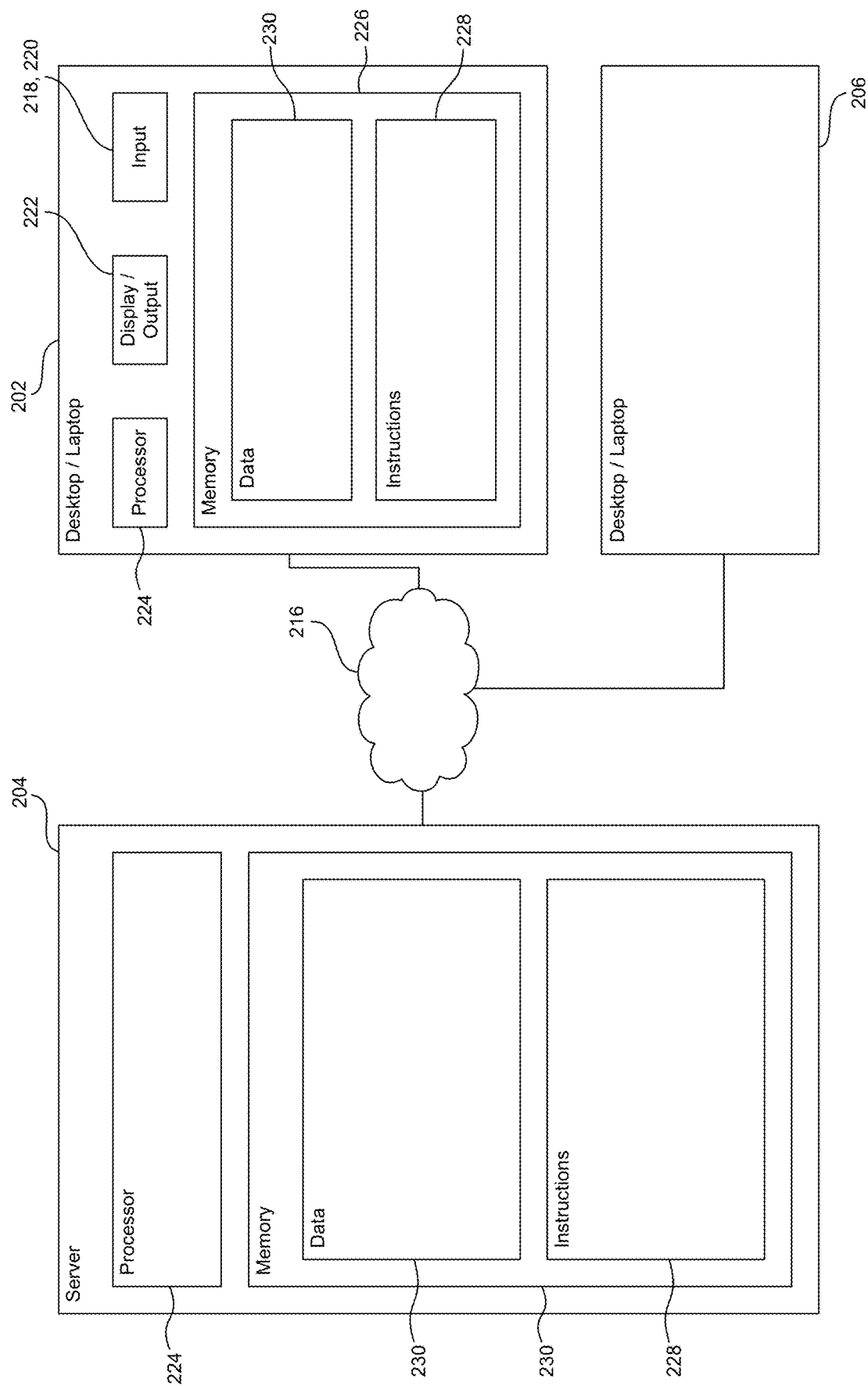
FIG. 2C shows computing devices that may be used in accordance with an aspect of the technology of the present application.

Each computing device can include, for example, one or more computers having user inputs such as a keyboard and mouse and/or various other types of input devices such as pen-inputs, joysticks, buttons, touch screens, etc., as well as a display, which could include, for instance, a CRT, LCD, plasma screen monitor, TV, projector, etc. Each computer 202, 204 and 206 may be a personal computer, server, etc. By way of example only, computer 202 may be a desktop computer, while computer 204 may be a server, and computer 206 may be a laptop. As shown in FIG. 2C each computer, such as computers 202 and 204, contains a processor 224, memory 226 and other components typically present in a computer.

With continued reference to FIG. 2C, memory 226 stores information accessible by processor 224, including instructions 228 that may be executed by the processor 224 and data 230 that may be retrieved, manipulated or stored by the processor. The memory may be of any type capable of storing information accessible by the processor, such as a hard-drive, ROM, RAM, CD-ROM, DVD, Blu-Ray disk, flash memories, write-capable or read-only memories. The processor 224 may comprise any number of well known processors, such as processors from Intel Corporation. Alternatively, the processor may be a dedicated controller for executing operations, such as an ASIC.

The instructions 228 may comprise any set of instructions to be executed directly (such as machine code) or indirectly (such as scripts) by the processor. In that regard, the terms "instructions," "steps" and "programs" may be used interchangeably herein. The instructions may be stored in any computer language or format, such as in object code or modules of source code. The functions, methods and routines of instructions in accordance with the present invention are explained in more detail below.

Data 230 may be retrieved, stored or modified by processor 224 in accordance with the instructions 228. The data may be stored as a collection of data. For instance, although the invention is not limited by any particular data structure, the data may be stored in computer registers, in a relational database as a table having a plurality of different fields and records, XML documents, or flat files. Map-type image data may be stored in flat files such as keyhole flat files ("KFF"). Content and advertising data may be stored in one or more relational databases.

The data may also be formatted in any computer readable format such as, but not limited to, binary values, ASCII etc. Similarly, the data may include images stored in a variety of formats such as vector-based images or bitmap images using lossless (e.g., BMP) or lossy (e.g., JPEG) encoding. Moreover, the data may include any information sufficient to identify the relevant information, such as descriptive text, proprietary codes, pointers, references to data stored in other memories (including other network locations) or information which is used by a function to calculate the relevant data.

Although the processor 224 and memory 226 are functionally illustrated in FIG. 2C as being within the same block, it will be understood that the processor and memory may actually comprise multiple processors and memories that may or may not be stored within the same physical housing or location. For example, some or all of the instructions and data may be stored on a removable recording medium such as a CD-ROM, DVD or Blu-Ray disk. Alternatively, such information may be stored within a read-only computer chip. Some or all of the instructions and data may be stored in a location physically remote from, yet still accessible by, the processor. Similarly, the processor may actually comprise a collection of processors which may or may not operate in parallel. Data may be distributed and stored across multiple memories 126 such as hard drives, data centers, server farms or the like.

In one aspect, the computing device 204 comprises a server. The other computing devices 202, 206 computer may be a general purpose computer, intended for use by a person, having all the components normally found in a personal computer such as a central processing unit ("CPU"), display, CD-ROM, DVD or Blu-Ray drive, hard-drive, mouse, keyboard, touch-sensitive screen, speakers, microphone, modem and/or router (telephone, cable or otherwise) and all of the components used for connecting these elements to one another.

The server and computers are capable of direct and indirect communication with other computers, such as over network 216. The network 216, including any intervening nodes, may comprise various configurations and protocols including the Internet, intranets, virtual private networks, wide area networks, local networks, private networks using communication protocols proprietary to one or more companies, Ethernet, WiFi, Bluetooth and HTTP.

Communication across the network, including any intervening nodes, may be facilitated by any device capable of transmitting data to and from other computers, such as modems (e.g., dial-up or cable), network interfaces and wireless interfaces. Server 204 may be an application server such as a web server.

Although certain advantages are obtained when information is transmitted or received as noted above, other aspects of the invention are not limited to any particular manner of transmission of information. For example, in some aspects, the information may be sent via a medium such as a disk, tape, CD-ROM, DVD, Blu-Ray disk or directly between two computer systems via a dial-up modem. In other aspects, the information may be transmitted in a non-electronic format and manually entered into the system.

The networked architecture 260 shown in FIG. 2B provides some flexibility in implementing the system. For example, the more complex processing may be done on the server 204, while the computer 202 may be used to control the actual acquisition of magnetic resonance signals from the apparatus 100. For example, the server may, in accordance with the discussions below, process the magnetic resonance signals it receives from computer 202 to identify the anatomy of interest and cerebro-spinal anatomy and then instruct the computer 202 to perform measurements of the CSF using the identified anatomy of interest and cerebro-spinal anatomy. Alternatively, the system may be simplified architecturally as shown in FIG. 2A with only a computer, such as computer 204, more directly connected to the apparatus 100 and performing all the analysis, while at the same time controlling the apparatus 100.

Databases 1 and 2 are preferably used to store patient data, such as images resulting from MRI scans. The databases may also be used to store other data, as well as the computer code or instructions that the server and/or computers use to perform the measurements and methods disclosed herein.

In accordance with an aspect of the present technology, those measurements and methods include a software capability that detects and constructs outlines of anatomy of interest that allow for accurate and reproducible identification of anatomies of interest and measurement of CSF flow. Phase-contrast MRI pulse sequences provide the capability to visualize and measure the flow of CSF. The phase-contrast pulse sequence creates images with pixel intensities that correspond to flow velocities. Conversion factors may be used to convert pixel intensity in MRI images into absolute CSF flow velocities. In addition to flow velocities, flow rates, volume and pressure gradients of the CSF may also be computed based on the pixel intensity.

In a method in accordance with the present technology, a portion of the cerebro-spinal anatomy of a subject is selected for magnetic resonance imaging. The cerebro-spinal anatomy may include any one of the ventricles, the spinal cord, mid-C2 vertebral level, the cerebral aqueduct (or Aqueduct of Sylvius), spinal canal, the sub-arachnoid space, the epidural space, the cerebello-medullary cistern, foramen of Monro, foramen of Magendie, foramen magnum, and so on down to the lumbar spine, i.e., anywhere that CSF is flowing. Once the region of interest of the cerebro-spinal anatomy is selected, e.g., by a user, a phase contrast MRI pulse sequence is then acquired of the region using apparatus 100. Acquisition of the MRI pulse sequence results in the acquisition of MRI data or signals. In accordance with aspect of this technology, acquisition of this MRI data or signal may be coordinated with cardiac signals of the user. In some instances, acquisition of the MRI data may be triggered by signals generated by an electrocardiogram device. Such a device will typically be coupled to subject at regions where a cardiac signal may be detected. This cardiac signal may then be used to trigger the acquisition of images, or control on or off cycling of the pulse sequence. Alternatively, the MRI signals or data may be obtained while capturing the cardiac cycle data. In this respect, the cardiac cycle trigger signal need not be used to actually trigger acquisition of the MRI signals. Rather, the MRI signals or data and cardiac trigger signals or data need only be recorded together. With both signals recorded, the processor may then retrospectively synthesize the MRI images by using the timestamps of the cardiac trigger signals to reorder the MRI data. In this way, MRI data or signal acquisition need not be synchronized with the subject's cardiac cycle.

Figure 3:
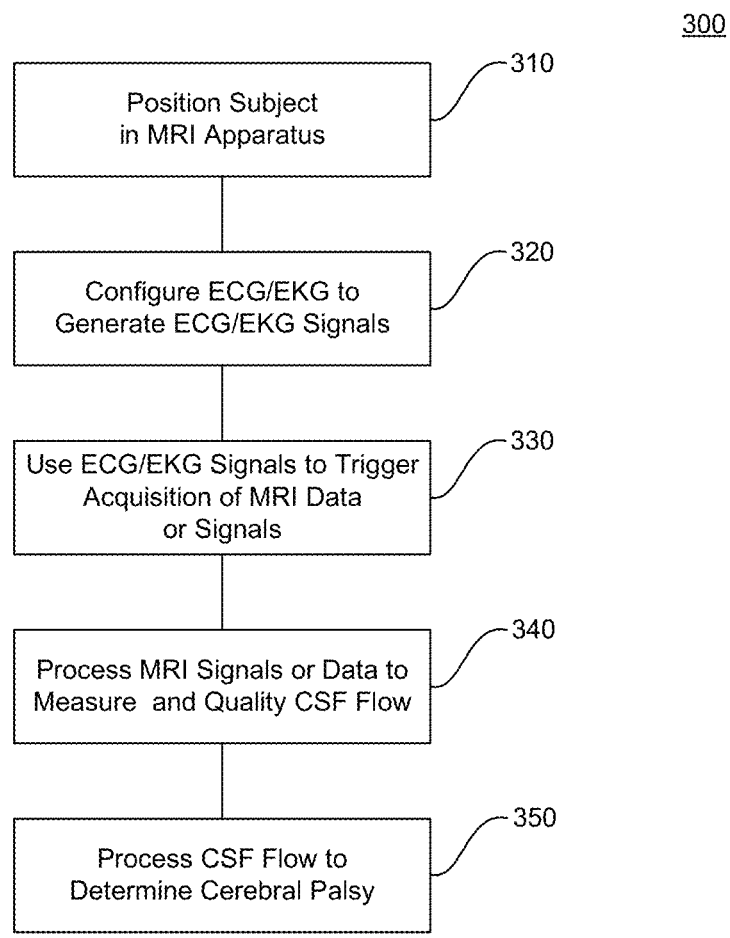
FIG. 3 shows method steps in accordance with an aspect of the technology of the present application.

In a more specific example as shown in FIG. 3, the method 300 is explained with the region of interest being the spinal cord. The method begins with the subject being positioned in the MRI apparatus, step 310, such as for example the apparatus of FIG. 1. The subject may be an adult or a neonate. If a neonate, the subject may be positioned in a car seat or on the lap of an adult.

Next the subject may be equipped with an electrocardiogram ("ECG" or "EKG") device and the EKG is configured to obtain EKG signals from the subject, step 320. EKG signals represent cardiac activity and CSF flow is pulsatile flow that follows the cardiac cycle. As such the EKG signals carry information about the triggering of the cardiac cycle. At step 330, the EKG signal timestamp the MRI signals or trigger acquisition of the MRI signals or scans of the spinal cord region. In lieu of an ECG or EKG, the patient may be equipped or fitted with any device capable of detecting the cardiac cycles. Such devices include not only an electrocardiogram but also a plethysmograph or an ultrasound cardiogram. The plethysmograph is considered convenient as it may be attached to a subject's finger. In contrast, the other devices may require more leads to be coupled to the subject or cumbersome to use. In any event, functionally, any device that can provide a trigger signal that is associated with the cardiac cycle may comprise the cardiac trigger device.

At step 340, the scans or signals are processed, for example by the computers described in FIG. 2C, as part of either system shown in FIG. 2A or 2B, to measure and quantify the CSF flow. With phase contrast MRI, CSF flow in, for example, both the Sagittal and Axial planes can be imaged or acquired. Such imaging technique or data acquisition provides both quantitative and qualitative information about CSF flow. The measurement and/or quantification of CSF flow may comprise a software capability that detects and constructs outlines of anatomy of interest that allow for accurate and reproducible identification of anatomies of interest and measurement of CSF flow. Phase-contrast MRI pulse sequences provide the capability to visualize and measure the flow of CSF. The phase-contrast pulse sequence creates images with pixel intensities that correspond to flow rates or velocities. Conversion factors may be used to convert pixel intensity in a region of interest in MRI images into absolute CSF flow rates or velocities. In addition to flow rates or velocities, volume and pressure gradient of the CSF may also be computed based on the pixel intensity as function of time. The method also includes, separately or in conjunction with the foregoing processes, selecting a region of interest of the cerebro-spinal anatomy and identifying a center point or central location within the region of interest. Using the center point or central location, the intensity of image pixels resulting from the phase contrast scan is then compared to intensity thresholds to determine the interior and exterior outlines of the region of interest bordering the CSF flow. The center point or central location may also be determined manually. Once the outlines are determined, the CSF flow can be determined using conversion factors that convert pixel intensity into flow rates for those pixels within the region defined by the outlines.

The CSF flow measurements may comprise any one of a peak systolic CSF velocity, a peak diastolic CSF velocity (e.g., cm/sec), a peak systolic CSF flow, a peak diastolic CSF flow (e.g., cc/sec), a peak systolic pressure gradient, a peak diastolic pressure gradient, a peak-to-peak pressure gradient (e.g., mmHg/cm) cinematic representations of CSF flow (e.g., movies), or measurements of CSF area (e.g., $cm^2$). These CSF flow measurements may be used in part to assess a subject's risk or likelihood of having cerebral palsy. For instance, in many brain abnormalities, including cerebral palsy, one may assess leakage of CSF (for instance, due to a buildup of intracranial pressure) based on low measured CSF velocities and low CSF pressure gradients, as compared to measurements taken in normal subjects having no CSF leakage. A diffusion weighted MRI technique can be also used to assess the leakage of CSF.

Additionally, leakage of CSF fluid into the surrounding brain tissue may be indicated by an relatively large area of a CSF region, or a relatively large area of CSF, compared to measurements taken in normal subjects having no CSF leakage. The CSF area measurements may also be used to augment the assessment of the risk of cerebral palsy. Early detection of such lesions is also possible by diffusion weighted MRI. The region of interest of measurement may comprise various locations of the CSF circulatory system including for example, the spinal cord, mid-C2 vertebral level and Aqueduct of Sylvius.

Example measurements of a subject being screened for CP (hereinafter, the "CP subject") and of normal subjects are shown in Table 1. The measurements were derived from upright imaging of each of the subjects. In particular, Table 1 shows the CSF flow measurements of one CP subject that is being scanned for cerebral palsy at birth, and average CSF flow measurements of 19 normal subjects that are not suspected of having cerebral palsy. Table 1 also shows the range of values of the CSF flow measurements for the normal subjects within about one standard deviation of the mean. This range is referred to herein as the "67% interval." The respective ranges of values of Table are taken as normal ranges of CSF flow measurement values for a group of normal subjects. Table 1 also indicates whether the CP subject's measurements fall within, above, or below the 67% interval range, which in turn indicates whether the CP subject's measurements fall within the normal range of CSF flow measurement values.

TABLE 1

| Measurement Type | CP Subject Measurement | Within Limits? | 19 Normal Subjects (67% Interval) | | |
|---|---|---|---|---|---|
| | | | Mean − σ | Mean | Mean + σ |
| Peak systolic CSF flow, cc/s | 2.49765 | Normal | 2.2267293 | 2.8825479 | 3.5383665 |
| Peak diastolic CSF flow, −cc/s | −0.831011 | Normal | 0.7084565 | 1.0174888 | 1.3265211 |
| Peak systolic CSF velocity, cm/s | 0.675897 | Low | 0.8551304 | 1.1695652 | 1.484 |
| Peak diastolic CSF velocity, −cm/s | −0.224883 | Low | 0.2751727 | 0.4078395 | 0.5405063 |
| Peak-to-peak pressure gradient, mmHg/cm | 0.0136935 | Low | 0.0166542 | 0.0232362 | 0.0298183 |
| Peak systolic pressure gradient, mmHg/cm | 0.008495 | Low | 0.0101951 | 0.0149155 | 0.0196358 |
| Peak diastolic pressure gradient, −mmHg/cm | −0.0051985 | Low | 0.0060766 | −0.0083208 | 0.0105649 |
| Area of CSF space, cm^2 | 3.69531 | High | 1.9096616 | 2.5668189 | 3.2239763 |

As can be seen in Table 1, peak systolic and diastolic CSF flow of the CP subject were observed to fall within one standard deviation of the average peak systolic and diastolic CSF flow values of 19 normal subjects, respectively. Therefore, based solely on the peak CSF flow measurements, there is no indication of the CP subject having a risk of cerebral palsy. However, peak systolic and diastolic CSF velocities of the CP subject were observed to be greater than a standard deviation below the average peak systolic and diastolic CSF velocities of the normal subjects, respectively. Therefore, the peak CSF velocity measurements could be an indicator of cerebral palsy. Additionally, peak-to-peak, peak systolic and peak diastolic pressure gradients of the CP subject were observed to be greater than a standard deviation below the average peak-to-peak, peak systolic and peak diastolic pressure gradients of the normal subjects, respectively. Therefore, the pressure gradient measurements are another possible indicator of cerebral palsy. Additionally, CSF area of the CP subject was observed to be greater than a standard deviation above of the average CSF area of the normal subjects. Therefore, the CSF area measurements is yet another possible indicator of cerebral palsy.

At step 350, the CSF flow is used to assess Cerebral Palsy. The assessment includes comparing the various collected CSF flow measurements, such as flow rate, flow velocity, pressure gradients, and CSF area, of the subject to the ranges of CSF flow measurements of the normal or control subjects that are not suspected of having cerebral palsy. Normal subjects are expected to have CSF flow measurements that fall within a standard deviation The normative values thus comprise thresholds which the processor may then use to assess cerebral palsy.

Continuing with the example of Table 1, assuming for the sake of example that the likelihood of falling outside of the 67% interval for each indicator is independent of one another, then a likelihood of falling outside of the 67% interval for a given number "x" of indicators can be determined according to a binomial distribution. In this manner, statistically speaking, it may be normal for a given subject to fall outside the 67% interval for one or two or even three of the above measurements. Therefore, a few single CSF measurements of the CP subject falling outside the 67% interval would not be statistically significant and would not significantly increase a risk of the CP subject having cerebral palsy. However, multiple CSF measurements of the CP subject falling outside the 67% interval may be statistically significant and may indicate an increased risk or likelihood of the CP subject having cerebral palsy. For instance, the odds of a subject falling outside of the 67% interval for at least four out of eight of the measurements is only 25%. In the case shown in Table 1, in which the tested CP subject fell outside of the 67% interval for five out of eight of the measurements, the likelihood of at least this many of the measurements falling outside the 67% interval was only 8.5%, which is a good indication of an anomaly in the subject's measurements that requires further examination. By extension, a subject falling outside of the 67% interval for even more measurements would be even less likely (1.9% for at least six out of eight measurements, 0.2% for at least seven out of eight measurements, and 0.01% for all eight measurements), and the measurements would be an even greater indication of a risk of the subject having cerebral palsy.

The above example uses a 67% interval to define a range of normal measurements. However, other intervals may be used in order to define ranges of normal values. For instance, a wider interval could be used if a relatively small number of parameters are evaluated, or a narrower interval could be used if a relatively large number of parameters are evaluated. Additionally, the same range or interval does not need to be used for every evaluated parameter.

It should be recognized that CSF measurements are not the only information on which an assessment of cerebral palsy may be based. To the contrary, the CSF measurements may be one piece of information on which the assessment of cerebral palsy may be based. Hence, the CSF measurements are described herein as providing an indication of a risk of cerebral palsy, but not a direct indication of cerebral palsy itself. As such, determining that a patient is at risk of cerebral palsy does not necessarily mean that the patient is immediately treated as having cerebral palsy or treated for cerebral palsy. Instead, determining that a patient is at risk of cerebral palsy may indicate the need for further testing, whereas such testing would not be prescribed absent the indication of a risk of cerebral palsy. Such testing may include, but is not limited to a neurological examination of the patient.

Figure 4:
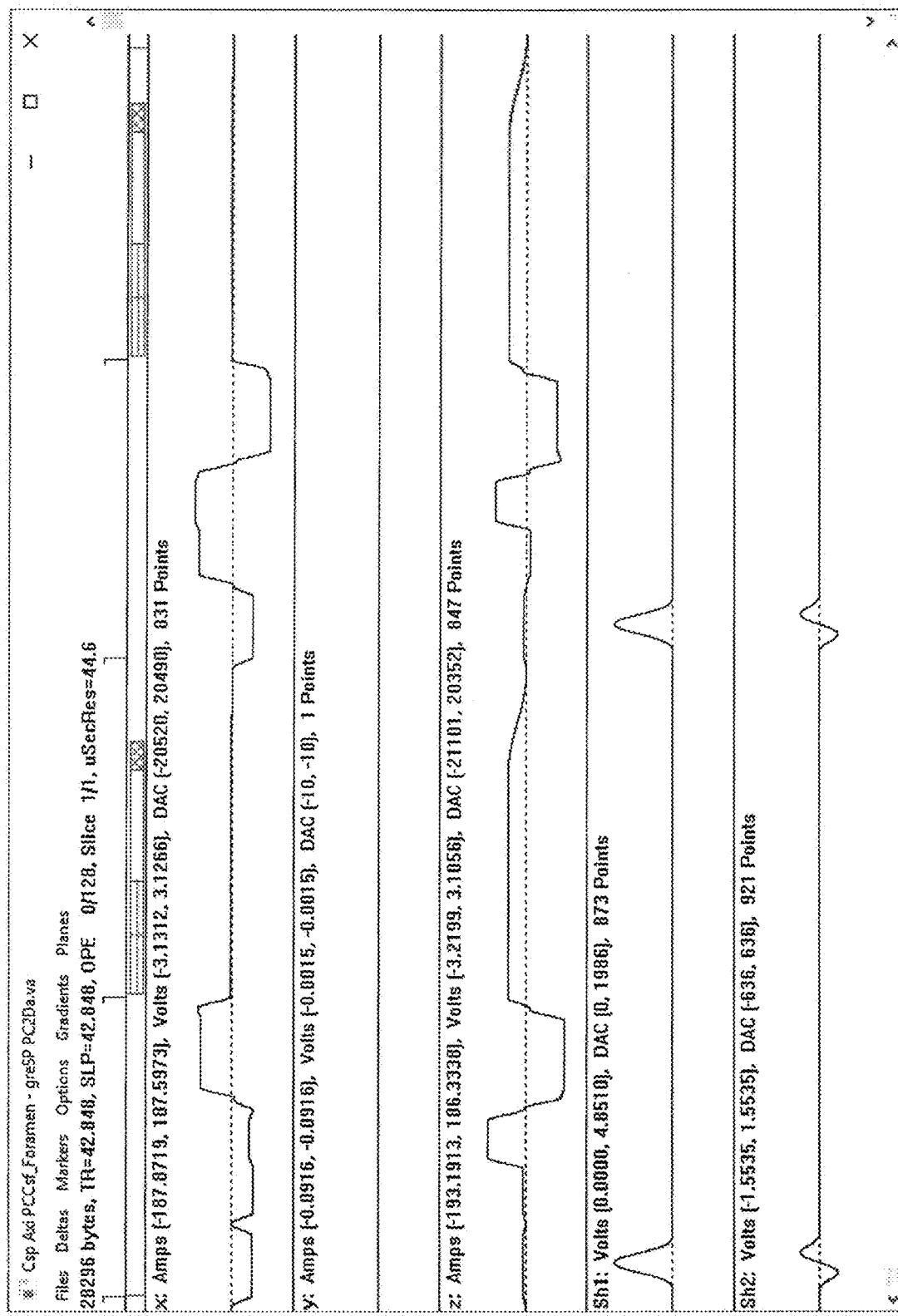
FIG. 4 shows an example of phase contrast pulse sequence in accordance with an aspect of the technology of the present application.

FIG. 4 shows an example of a typical phase contrast pulse sequence, which may be used to obtain flow information related to CSF.

In an example of use, a scan was acquired. The scan consisted of 32 individual images taken to represent all parts of the cardiac cycle. The images were collected in a format that supports display of the images in a time-ordered sequence, such as a cine format. These 32 images were then played back in the form of a movie. The region of interest was then selected, for example, by processing intensity data associated with pixels to determine a region where a CSF flow measurement might be made or determined. The region of interest may alternatively be selected by a user. Once the region of interest is selected an outline area is determined. The inner boundary of that outline area is then used to measure or calculate CSF flow.

Figure 5B:

FIGS. 5A and 5B show images of a subject with cerebral palsy in accordance with the present technology. FIG. 5A shows two images of a patient with Cerebral Palsy, taken with different image contrast. The images show ventricles largely dilatated, along with a compressed brain matter region. FIG. 5B shows a coronal image of the same patient as shown in FIG. 5A. By using the technique of measuring CSF flow and using a cardiac trigger, a system can be developed that can determine cerebral palsy (CP). In addition to a magnetic resonance imaging system ("MRI system") and associated EKG circuitry, the system may also include a processor and associated instructions or software that control the MRI system and EKG circuitry to take images of the CSF flow.

In accordance with the foregoing description, aspects of present technology include:

A Cerebro-Spinal fluid (CSF) measurement method for assessing the risk of Cerebral Palsy, comprising positioning a patient in a magnetic resonance imaging (MRI) system in order to obtain magnetic resonance measurements of the CSF, attaching an ECG, EKG, plethysmograph, or ultrasound cardiogram or other cardiac cycle measuring device to the patient, using a signal generated by the EKG measuring device to trigger acquisition of magnetic resonance data from the patient, using the magnetic resonance data to measure CSF flow, and comparing the CSF flow measurements of the patient with CSF flow thresholds. The thresholds may comprise measurements from people not at risk for Cerebral Palsy in order to assess the patient's risk of Cerebral Palsy.

An EKG measuring device that is MRI-compatible.
An MRI system capable of positioning the patient for upright imaging.
AN MRI system capable of positioning the patient for recumbent imaging.
An MRI system capable of positioning the patient for multi-position imaging.
The CSF flow measurement comprising velocity (e.g. cm/sec.), flow (e.g. cc/sec) or cinematic representations of CSF flow (e.g. movies).
Measuring CSF flow using a Diffusion-Weighted MRI technique.
Measuring CSF flow at various locations in the CSF circulatory system comprising the spinal cord, mid-C2 vertebral level, and the Aqueduct of Sylvius.

The present technology may find use in the following situations:
Where the patient is a neonate.
Where the patient is a neonate positioned in the magnetic resonance imaging system sitting in the lap of an adult.
Where the patient is a neonate positioned in the MRI system seated in a car seat compatible with the requirements for MRI.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for assessing a risk for cerebral palsy in a subject, comprising:
   acquiring magnetic resonance imaging data of a selected region of interest of the subject's anatomy by the magnetic resonance imaging apparatus;
   measuring CSF flow using the acquired magnetic resonance imaging data to obtain one or more CSF flow measurements; and
   processing the acquired magnetic resonance imaging signals to assess the risk of cerebral palsy in the subject, wherein the processing includes: for each CSF flow measurement of the one or more CSF flow measurements, the processing includes determining whether the CSF flow measurement is within a predetermined range of a corresponding CSF flow measurement value associated with subjects that do not have an elevated risk cerebral palsy.

2. The method of claim 1 further comprising receiving one or more signals from a cardiac triggering device coupled to the subject, wherein the cardiac triggering device comprises any one of an electrocardiogram, plethysmograph, or ultrasound cardiogram.

3. The method of claim 1, wherein the CSF flow measurements include any one or combination of peak systolic CSF flow velocity, peak diastolic CSF flow velocity, peak systolic CSF flow rate, peak diastolic CSF flow rate, peak-to-peak pressure gradient, peak systolic pressure gradient, peak diastolic pressure gradient, and CSF area.

4. The method of claim 3, wherein the one or more CSF flow measurements is a plurality of CSF flow measurements, and wherein the processing includes determining a total number of the plurality of CSF flow measurements that are outside the respective predetermined ranges of CSF flow measurement values, wherein a greater number of CSF flow measurements being outside the respective predetermined ranges of CSF flow measurement values is indicative of a greater likelihood of the risk of cerebral palsy in the subject.

5. The method of claim 1, wherein processing the acquired magnetic resonance imaging signals comprises processing the CSF flow measurements as a sequence of images for display.

6. The method of claim 1, wherein the subject is positioned in one of a Trendelburg position, a reverse-Trendleburg position, an upright position or a recumbent position in the magnetic resonance imaging apparatus.

7. The method of claim 1, wherein the subject is a neonate seated in a car seat compatible with the magnetic resonance imaging apparatus.

8. The method of claim 3, wherein the cerebro-spinal anatomy comprises one or more locations in the CSF circulatory system.

9. The method of claim 8, wherein the CSF circulatory system comprises any one of the spinal cord, mid-C2 vertebral level and the Aqueduct of Sylvius.

10. A system for assessing a risk of cerebral palsy in a subject, comprising
    a magnetic resonance imaging apparatus configured to trigger acquisition of magnetic resonance imaging signals of a selected region of interest of the subject's anatomy based on the cardiac cycle triggering signals;
    a memory storing instructions; and
    a processor programmed using the instructions and configured to:
    receive the acquired magnetic resonance imaging signals,
    measure CSF flow using the acquired magnetic resonance imaging data to obtain one or more CSF flow measurements, and
    for each CSF flow measurement of the one or more CSF flow measurements, determine whether the CSF flow measurement is within a predetermined range of a corresponding CSF flow measurement value associated with subjects that do not have an elevated risk cerebral palsy.

11. The system of claim 10, wherein the processor is configured to measure any one or combination of peak systolic CSF flow velocity, peak diastolic CSF flow velocity, peak systolic CSF flow rate, peak diastolic CSF flow rate, peak-to-peak pressure gradient, peak systolic pressure gradient, peak diastolic pressure gradient, and CSF area.

12. The system of claim 11, wherein the one or more CSF flow measurements is a plurality of CSF flow measurements, and wherein the processors are configured to determine a total number of the plurality of CSF flow measurements that are outside the respective predetermined ranges of CSF flow measurement values, wherein a greater number of CSF flow measurements being outside the respective predetermined ranges of CSF flow measurement values is indicative of a greater likelihood of the risk of cerebral palsy in the subject.

13. The system of claim 10, wherein the processors is configured to process the CSF flow measurements for display as a sequence of images.

14. The system of claim 10, wherein the apparatus includes a pair of magnetic poles spaced apart along a first direction parallel to a support surface of the apparatus, wherein the magnetic poles are configured to create a magnetic field in the first direction, and wherein the apparatus is adapted to accommodate the subject between the poles while the subject is in an upright position.

15. The system of claim 14, wherein the apparatus is adapted to accommodate the subject while the subject is positioned in a Trendelburg position, a reverse-Trendleburg position, an upright position or a recumbent position.

16. The system of claim 14, wherein the apparatus is adapted to accommodate a neonate subject while the subject is positioned is seated in a car seat compatible with the magnetic resonance imaging apparatus.

17. The system of claim 12, wherein the selected region of interest in the subject's anatomy comprises one or more locations in the CSF circulatory system.

18. The system of claim 17, wherein the CSF circulatory system comprises any one of the spinal cord, mid-C2 vertebral level and the Aqueduct of Sylvius.

19. The system of claim 10, further comprising a triggering device coupled to the subject and configured to generate cardiac cycle triggering signals associated with a timing of the subject's cardiac function, wherein the cardiac triggering device comprises any one of an electrocardiogram, plethysmograph, or ultrasound cardiogram.

20. A method for assessing risk for cerebral palsy in a subject, comprising:
    acquiring magnetic resonance imaging data of a selected region of interest of the subject's anatomy by the magnetic resonance imaging apparatus, the selected region of interest comprising the cerebro-spinal anatomy;
    obtaining one or more CSF flow measurements from the acquired magnetic resonance imaging data, wherein the one or more CSF flow measurements includes one or more of CSF flow rate data, CSF flow velocity data, and pressure gradient data;
    comparing the obtained one or more CSF flow measurements to respective predetermined ranges of CSF flow measurement values to assess cerebral palsy, wherein the comparing comprises:
        for each CSF flow measurement of the one or more CSF flow measurements, the processing includes determining whether the CSF flow measurement is within a predetermined range of a corresponding CSF flow measurement value associated with subjects that do not have an elevated risk cerebral palsy.

21. The method of claim 20, wherein the CSF flow measurements include two or more of peak systolic CSF flow velocity, peak diastolic CSF flow velocity, peak systolic CSF flow rate, peak diastolic CSF flow rate, peak-to-peak pressure gradient, peak systolic pressure gradient, peak diastolic pressure gradient, and CSF area.

22. The method of claim 21, wherein the one or more CSF flow measurements is a plurality of CSF flow measurements, and wherein comparing the obtained CSF flow measurements to respective predetermined ranges of CSF flow measurement values comprises determining a total number of the plurality of CSF flow measurements that are outside the respective predetermined ranges of CSF flow measurement values, wherein a greater number of CSF flow measurements being outside the respective predetermined ranges of CSF flow measurement values is indicative of a greater likelihood of the risk of cerebral palsy in the subject.

23. The method of claim 20, wherein each predetermined range of a CSF flow measurement value is a 67% interval, whereby boundaries of the range are one standard deviation from a mean of the CSF flow measurement value measured in control subjects that are not suspected of having cerebral palsy.

* * * * *